United States Patent
Lee et al.

(10) Patent No.: US 7,485,762 B2
(45) Date of Patent: Feb. 3, 2009

(54) METHOD FOR PREPARING STYRENIC OLEFINS

(75) Inventors: Min-hyung Lee, Daejeon (KR); Sun-woo Lee, Daejeon (KR); You-mi Jeong, Daejeon (KR); Doh-yeon Park, Daegu (KR); Jin-young Ryu, Busan (KR)

(73) Assignee: LG Chem, Ltd. (KR)

( * ) Notice: Subject to any disclaimer, the term of this patent is extended or adjusted under 35 U.S.C. 154(b) by 512 days.

(21) Appl. No.: 10/556,962

(22) PCT Filed: Oct. 13, 2004

(86) PCT No.: PCT/KR2004/002613

§ 371 (c)(1),
(2), (4) Date: Nov. 16, 2005

(87) PCT Pub. No.: WO2005/035468

PCT Pub. Date: Apr. 21, 2005

(65) Prior Publication Data

US 2007/0032669 A1 Feb. 8, 2007

(30) Foreign Application Priority Data

Oct. 13, 2003 (KR) .................. 10-2003-0071139

(51) Int. Cl.
*C07C 1/20* (2006.01)

(52) U.S. Cl. ................................... 585/469

(58) Field of Classification Search ............ 585/469
See application file for complete search history.

(56) References Cited

U.S. PATENT DOCUMENTS

| 3,526,674 A | 9/1970 | Becker et al. |
| 4,273,622 A | 6/1981 | Becker ................ 203/28 |
| 4,521,637 A | 6/1985 | Stevens .............. 568/659 |

FOREIGN PATENT DOCUMENTS

| JP | 56-95132 A | 8/1981 |
| JP | 56-140935 A | 11/1981 |
| WO | WO 99/42426 A1 | 8/1999 |
| WO | WO 99/58480 A1 | 11/1999 |

OTHER PUBLICATIONS

Nishiguchi, T.: Kamio, C.J. Chem. Soc. Perkin Trans., 1, 1989, ppp. 707-710.
Nishiguchi, T.; Machida, M.; Yamaoto, E. Tetrachedron Lett., 1987, vol. 28, No. 39, pp. 4565-4568.
PCT International Search Report; International Application No. PCT/KR2004/002613; International Filing Date: Oct. 13, 2004; Date of Mailing: Jan. 17, 2005.

*Primary Examiner*—Thuan Dinh Dang
(74) *Attorney, Agent, or Firm*—Cantor Colburn LLP

(57) ABSTRACT

The present invention relates to a method for preparing a styrenic olefin. The method of the present invention comprises the steps of: adding a catalyst and a solvent in a reactor and heating the reactor to create a reflux state; adding an alcohol starting material to the reactor dropwise at a constant rate; removing water generated by adding the alcohol starting material from the reactor, and purifying the obtained styrenic olefin. The method of the present invention is advantageous in minimizing byproducts and preparing styrenic olefins having a variety of substituents in high yield.

14 Claims, No Drawings

METHOD FOR PREPARING STYRENIC OLEFINS

TECHNICAL FIELD

The present invention relates to a method for preparing a styrenic olefin. More particularly, the present invention relates to a method for preparing a styrenic olefin with a variety of substituents in high yield by performing alcohol dehydration at an elected temperature in the presence of a catalyst and a solvent.

BACKGROUND ART

Styrene and styrenic olefins are important materials used for a variety of applications, from organic synthesis of medicines, natural products, etc. to preparation of polystyrenic resins used in daily lives and industries. Especially, preparation of polystyrenic resins using styrenic olefins is industrially very important and is being actively investigated.

To take typical examples, there are homopolymers such as amorphous polystyrene (PS) resin, crystalline syndiotactic polystyrene (SPS), etc. and copolymers such as acrylonitrile-butadiene-styrene (ABS) resin, styrene-butadiene-styrene (SBS) resin, acrylonitrile-styrene-acrylate (ASA) resin, styrene-butadiene latex (SB latex), etc.

Researches on preparation of a variety of polystyrenic resins and researches on styrene and preparation of new styrenic olefins related with physical properties of polystyrenic resins are being performed and reported continuously.

Generally, styrene is prepared from dehydrogenation of ethylbenzene. In another method, 1-phenyl-ethanol is dehydrated to styrene using a dehydrating catalyst. So, most techniques are focusing on obtaining styrene from dehydration of 1-phenyl-ethanol.

The dehydration technique of 1-phenyl-ethanol known thus far can be performed both in gaseous and liquid phases. Non-homogeneous dehydrating catalysts comprising acidic materials can be used in both environments.

The most typical non-homogeneous dehydrating catalyst is a modified alumina It is the most frequently used in dehydration of 1-phenyl-ethanol. The dehydration condition for a liquid phase is usually 100-300° C. The usual gas phase dehydration condition is 210-330° C. and 0.1-10 atm.

WO 99/58,480 discloses dehydration under above conditions using catalysts with different particle sizes. U.S. Pat. No. 3,526,674 discloses dehydration in the presence of alumina catalysts and a variety of acidic catalysts. However, the reaction was successful only at an elevated temperature (200° C. or higher). Especially, preparation of styrenic olefins having substituents at a phenyl ring other than the styrene ring has never been reported.

Homogeneous catalysts are applicable only to the liquid phase. Of the homogeneous catalysts, p-toluenesulfonic acid is the most widely used. Cases of dehydrating 1-phenyl-ethanol to styrene under a mild liquid-phase condition using a catalyst obtained by adsorbing a metallic compound on silica gel were reported (*J. Chem. Soc. Perkin Trans.* I 1989, 707; *Tetrahedron Letters,* 1987, 28, 4565). But, when dehydration of alcohol was performed according to the methods presented in these papers, the reaction yield was not satisfactory (50% or less for most cases) and a lot of byproducts were generated.

Also, when the methods were applied to preparation of new styrenic olefins having substituents, such byproducts as ether dimer, oligostyrene, etc. were produced excessively. Because separation of these byproducts from styrenic olefin, or the target compound, is difficult, it raises an economic problem.

DISCLOSURE

In view of these problems, it is an aspect of the present invention to provide a method for preparing a styrenic olefin capable of minimizing by product generation, preparing a styrenic olefin having a variety of substituents and improving production yield.

It is another aspect of the present invention to provide a styrenic olefin having a variety of substituents.

In order to attain the aspects, the present invention provides a method for preparing a styrenic olefin comprising the steps of: adding a catalyst and a solvent to a reactor and heating the reactor to create a reflux state; adding an alcohol starting material dropwise to the reactor at a constant rate; removing water generated by adding the alcohol starting material from the reactor; and purifying the obtained styrenic olefin.

The catalyst may be at least one selected from the group consisting of acetic acid, haloacetic acid, phosphoric acid, hydrochloric acid, sulfuric acid and an alkylsulfonic acid, an arylsulfonic acid, an alkylarylsulfonic acid, a haloarylsulfonic acid, an alkylhaloarylsulfonic acid, an alkylcarboxylic acid, an arylcarboxylic acid, a haloalkylcarboxylic acid, a haloarylcarboxylic acid and an alkylhaloarylcarboxylic acid having 1-20 carbon atoms.

The catalyst may be comprised in 0.1-20 mol % per 100 mol % of the alcohol starting material.

The solvent may be at least one selected from the group consisting of an alkane, a cycloalkane, an arene, an alkylarene, a haloalkane, a halocycloalkane, a haloarene and an alkylhaloarene having 1-20 carbon atoms.

The alcohol starting material may be a compound represented by the following Formula 1:

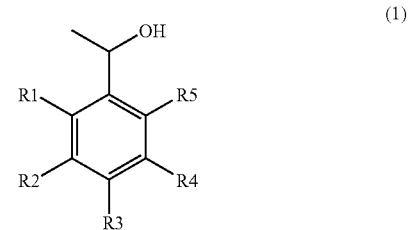

(1)

The content of the alcohol staring material may be 0.05-5 M.

The reflux state may be created at a temperature of 50-200° C.

The dropping time of the alcohol staring material may be 0.1-4 hours.

After dropping of the alcohol staring material is completed, the reaction may be performed for two hours or less.

The water may be removed by distilling or and/or using a drying agent.

The drying agent may be at least one selected from the group consisting of anhydrous magnesium sulfate (MgSO$_4$), anhydrous calcium sulfate (CaSO$_4$), anhydrous magnesium chloride (MgCl$_2$), anhydrous calcium chloride (CaCl$_2$), alumina (Al$_2$O$_3$) and silica gel (SiO$_2$).

The purification may be performed by distilling and/or passing through an alumina or a silica gel columns.

The distillation may be performed by simple distillation and/or vacuum distillation.

The distillation may be performed at a temperature of 25-400° C.

The distillation may be performed at a degree of vacuum of 0.5-10$^{-6}$ atm.

The present invention also provides a compound represented by the following Formula 2, which is prepared from the method:

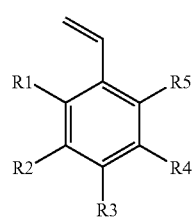

(2)

In Formula 1 and Formula 2, each of R1, R2, R3, R4 and R5, which may be identical or different, may be at least one selected from the group consisting of a hydrogen atom, a halogen group, a hydroxy group, a thio group, an amine group, an alkyl group, a cycloalkyl group, a haloalkyl group, an alkylsilyl group and a silylalkyl group, an alkoxy group, an alkylthio group, an alkylamine group having 1-20 carbon atoms and an aryl group, a haloaryl group, an arylalkyl group, an alkylaryl group, an arylsilyl group, a silylaryl group, an arylalkylsilyl group, an aryloxy group, an arylthio group and an arylamine group having 6-40 carbon atoms.

Hereunder is given a more detailed description of the present invention.

The present invention provides a novel method for preparing a styrenic olefin in high yield according to Scheme 1 below while minimizing byproducts by adjusting amount of the catalyst and the solvent:

[Scheme 1]

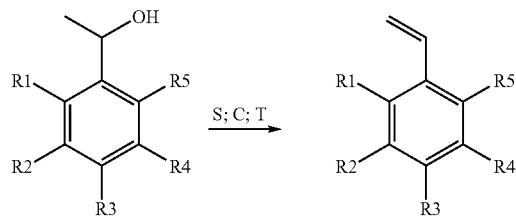

where S stands for a reaction solvent, C, an acidic catalyst and T, reaction temperature.

In Scheme 1, each of R1, R2, R3, R4 and R5, which may be identical or different, may be at least one selected from the group consisting of a hydrogen atom, a halogen group, a hydroxy group, a thio group, an amine group, an alkyl group, a cycloalkyl group, a haloalkyl group, an alkylsilyl group, a silylalkyl group, an alkoxy group, a alkylthio group and an akylamine group having 1-20 carbon atoms and an aryl group, a haloaryl group, an arylalkyl group, an alkylaryl group, an arylsilyl group, a silylaryl group, an arylalkylsilyl group, an aryloxy group, an arylthio group and an arylamine group having 6-40 carbon atoms.

In Scheme 1, the 1-phenyl-ethanol substituted on the benzene ring is dehydrated in liquid phase by an acidic catalyst to give a styrenic olefin. In the conventional reaction methods, the reaction yield is low because the intermolecular dehydration produces an ether dimer from substitution of the alcohol starting material present previously in the liquid phase or because the obtained styrenic olefin is oligomerized by the acidic catalyst as the concentration of the styrenic olefin increases according to the progress of the reaction or the extended reaction time.

In order to overcome such side reactions, the initial amount of the alcohol starting material should be low and the alcohol starting material should promptly react with the catalyst to generate a styrenic olefin. Because the amount of the catalyst in the reactor remains constant and the added amount of the alcohol starting material is much more than that, thereby occurring side reaction, the concentration of the alcohol should be maintained constantly.

And, because the concentration of the styrenic olefin increases with time, the amount of the solvent should be controlled to prevent oligomerization by the catalyst. Also, the reaction time should be minimized to prevent side reactions.

Lastly, since the water generated by the side reaction may react with the styrenic olefin in the presence of the catalyst to give the alcohol starting material, according to the reverse reaction of Scheme 1. Therefore, the water should be removed continuously.

In order to solve such problems and prepare a styrenic olefin in high yield and large quantity, a catalyst and a solvent are added to a reactor previously and heated to create a reflux condition. Then, an alcohol starting material is added dropwise slowly for a given time at a constant rate, while removing produced water from the reactor. Then, a styrenic olefin obtained from the reaction is purified.

According to the method of this invention, the catalyst is preferably comprised in 0.1-20 mol %, more preferably in 0.5-10 mol %, per 100 mol % of the alcohol starting material. If the content of the catalyst is below 0.1 mol %, dehydration proceeds slowly, so that unreacted alcohol starting material may remain. Otherwise, if it exceeds 20 mol %, the styrenic olefin generated from the initial reaction may be oligomerized by the catalyst.

The amount of the solvent is calculated from the amount of the alcohol starting material.

The alcohol starting material is dissolved in the reaction solvent. Preferably, the concentration of the alcohol starting material is 0.05-5 M, more preferably 0.1-1 M, although it may be different depending on its solubility in the reaction solvent. If the concentration of the alcohol starting material is below 0.05 M, the productivity becomes low because a large amount of solvent is required. Otherwise, if it exceeds 5 M, the concentration of the styrenic olefin product increases, thereby occurring oligomerization side reaction in the reactor and the solubility of the alcohol decreases, thereby remaining unreacted alcohol.

The reaction temperature is preferably 50-200° C., more preferably 50-150° C., although it may be different depending on the boiling point of the solvent . If the reaction temperature is below 50° C., dehydration does not proceed. Otherwise, if it exceeds 200° C., the styrenic olefin may be oligomerized in the reactor.

The alcohol starting material should be added to the reactor dropwise, as constantly as possible, preferably for 0.1-4 hours, more preferably for 0.5-2 hours. If the adding time is below 0.1 hour, unreacted alcohol starting material may form an ether byproduct. Otherwise, if the adding time is longer than 4 hours, the styrenic olefin produced in the initial reaction may be oligomerized.

After addition of the alcohol starting material, the reaction is preferably performed for 0.2 hours, more preferably for 0-0.5 hour. If the reaction is performed for longer than 2 hours, the reaction yield may be significantly low because of oligomerization of the styrenic olefin product.

The water, byproduct of the reaction, may be removed by distilling or using a drying agent which is added to the reactor in advance. Preferably, the drying agent is selected from anhydrous magnesium sulfate ($MgSO_4$), anhydrous calcium sulfate ($CaSO_4$), anhydrous magnesium chloride ($MgCl_2$), anhydrous calcium chloride ($CaCl_2$), alumina ($Al_2O_3$), silica gel ($SiO_2$), etc.

After the reaction is terminated, the solvent remaining in the reaction solution is removed by distillation and the remaining styrenic olefin product my be purified by (1) distilling or (2) filtering through an alumina or a silica gel columns.

The distillation is preferably performed by simple distillation or vacuum distillation, more preferably by vacuum distillation. The temperature for the simple distillation or vacuum distillation, although variable depending on the boiling point of the styrenic olefin, is preferably 25-400° C. and the degree of vacuum is preferably $0.5$-$10^{-6}$ atm. If the distillation temperature is below 25° C., the styrenic olefin is hardly vacuum-distilled. Otherwise, if it exceeds 400° C., deformation due to thermal polymerization of olefin, etc is occurred t distillation.

BEST MODE

Hereinafter, the present invention will be described in more detail through examples but the present invention is not limited to or by them.

EXAMPLE 1

Preparation of Styrene Represented by Formula 3

An adequate amount of P-toluenesulfonic acid was dissolved in a two-neck flask containing toluene. A Dean-Stark trap and a dropping funnel were installed. Then, a 1.0 M 1-phenyl-ethanol toluene solution was added through the dropping funnel. The toluene solution was heated from outside to create a reflux state. Then, an alcohol solution was slowly added dropwise through the dropping funnel at a constant rate, for a given time.

After addition of the alcohol solution was completed, heating was stopped and the reactor was cooled down. After adding anhydrous magnesium sulfate, filtration was performed. Then, the toluene solution was removed completely using a rotary evaporator. The obtained crude oil was dissolved in hexane to adjust a concentration of about 1.0 M. The hexane solution was filtered through a column filled with activated alumina, which had been prepared beforehand, and dried in vacuum to obtain transparent and colorless styrene represented by Formula 3 below.

The prepared styrene was identified by NMR and the result was as follows;

$^1$H NMR ($CDCl_3$): δ 5.22 (d, 1H), 5.72 (d, 1H), 6.70 (q, 1H), 7.31 (m, 3H), 7.39 (d, 2H)

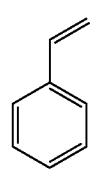

(3)

Table 1 below shows synthesis yield of styrene for each reaction condition.

TABLE 1

Preparation of styrene under a variety of conditions

| Run | Alcohol (M) | p-Toluenesulfonic acid (mol %) | Reaction temperature (° C.) | Addition time (hr) | Reaction time after addition (hr) | Yield (%) |
|---|---|---|---|---|---|---|
| 1 | 0.2 | 5 | 110 | 0.5 | 2 | 70 |
| 2 | 0.2 | 5 | 110 | 1 | 0.5 | 90 |
| 3 | 0.2 | 5 | 110 | 1.1 | 0 | 95 |
| 4 | 0.2 | 2 | 110 | 1.1 | 0 | 60 |
| 5 | 0.1 | 5 | 110 | 1.1 | 0 | 72 |
| 6 | 0.5 | 5 | 110 | 1.1 | 0 | 75 |

As seen in Table 1, a quite high production yield of styrene of 95% or more was obtained when 5 mol % of p-toluenesulfonic aid catalyst was used per 100 mol % of the alcohol starting material in the presence of 0.2 M of the reaction solution and the alcohol starting material was added dropwise at 110° C. for 1 hour and more (Run 3).

EXAMPLE 2

Preparation of p-n-butylstyrene Represented by Formula 4

A styrene represented by Formula 4 was prepared using 1-(p-n-butylphenyl)-ethanol in the same manner of Example 1 under the reaction condition given in Table 2 below.

The prepared styrene was identified by NMR and the result was as follows;

$^1$H NMR ($CDCl_3$): δ 0.75 (t, 3H), 1.15 (sextet, 2H), 1.41 (quintet, 2H), 2.41 (t, 2H) 5.01 (d, 1H), 5.52 (d, 1H), 6.52 (q, 1H), 6.97 (d, 2H), 7.17 (d, 2H)

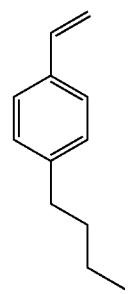

(4)

TABLE 2

Preparation of p-n-butylstyrene under a variety of conditions

| Run | Alcohol (M) | p-Toluenesulfonic acid(mol %) | Reaction temperature (° C.) | Addition time (hr) | Reaction time after addition (hr) | Yield (%) |
|---|---|---|---|---|---|---|
| 1 | 0.2 | 5 | 110 | 1.1 | 0 | 75 |
| 2 | 0.2 | 5 | 110 | 1.1 | 0.5 | 65 |
| 3 | 0.2 | 3 | 110 | 1.1 | 0 | 85 |
| 4 | 0.2 | 2 | 110 | 1.1 | 0 | 92 |
| 5 | 0.1 | 2 | 110 | 1.1 | 0 | 80 |
| 6 | 0.5 | 2 | 110 | 1.1 | 0 | 70 |

As seen in Table 2, the yield of p-n-butylstyrene was improved when the amount of p-toluenesulfonic acid was reduced to some degree (Run 4).

EXAMPLE 3

Preparation of p-n-hexylstyrene Represented by Formula 5

A styrene represented by Formula 5 was prepared using 1-(p-n-hexylphenyl)-ethanol in the same manner of Example 1 under the reaction condition given in Table 3 below.

The prepared styrene was identified by NMR and the result was as follows;

$^1$H NMR (CDCl$_3$): δ 0.88 (t, 3H), 1.28 (m, 6H), 1.60 (quintet, 2H), 2.58 (t, 2H), 5.18 (d, 1H), 5.68 (d, 1H), 6.69 (q, 1H), 7.13 (d, 2H), 7.30 (d, 2H)

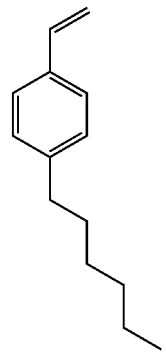

(5)

TABLE 3

Preparation of p-n-hexylstyrene under a variety of conditions

| Run | Alcohol (M) | p-Toluenesulfonic acid(mol %) | Reaction temperature (° C.) | Addition time (hr) | Reaction time after addition (hr) | Yield (%) |
|---|---|---|---|---|---|---|
| 1 | 0.2 | 2 | 110 | 1.1 | 0 | 80 |
| 2 | 0.2 | 1 | 110 | 1.1 | 0 | 75 |
| 3 | 0.1 | 2 | 110 | 0.5 | 0 | 92 |
| 4 | 0.1 | 5 | 110 | 0.5 | 0 | 70 |
| 5 | 0.5 | 2 | 110 | 0.5 | 0 | 63 |

As seen in Table 3, the result was similar to that of Example 2. However, the reaction yield was the highest when the concentration of the reaction solution and the reaction time were decreased in half (Run 3).

EXAMPLE 4

Preparation of n-cyclohexylstyrene Represented by Formula 6

A styrene represented by Formula 6 was prepared using 1-(p-n-cyclo-hexylphenyl)ethanol in the same manner of Example 1 under the reaction condition given in Table 4 below.

The prepared styrene was identified by NMR and the result was as follows;

$^1$H NMR (CDCl$_3$): δ 1.30 (m, 1H), 1.46 (m, 4H), 1.78 (m, 1H), 1.88 (m, 4H), 2.53 (s, 1H), 5.21 (d, 1H), 5.73 (d, 1H), 6.73 (q, 1H), 7.20 (d, 2H), 7.37 (d, 2H)

(6)

TABLE 4

Preparation of p-cyclohexylstyrene under a variety of conditions

| Run | Alcohol (M) | p-Toluenesulfonic acid(mol %) | Reaction temperature (° C.) | Addition time (hr) | Reaction time after addition (hr) | Yield (%) |
|---|---|---|---|---|---|---|
| 1 | 0.2 | 2 | 110 | 1.1 | 0 | 85 |
| 2 | 0.2 | 1 | 110 | 1.1 | 0 | 85 |
| 3 | 0.2 | 1.5 | 110 | 1.1 | 0 | 93 |
| 4 | 0.3 | 1.5 | 110 | 1.1 | 0 | 94 |
| 5 | 0.5 | 1.5 | 110 | 1.1 | 0 | 80 |

As seen in Table 4, the result was similar to that of Example 2. However, the yield was higher when a smiler amount of p-toluenesulfonic acid was used (Run 3). change in the initial concentration of the alcohol starting material had little effect on the final yield (Run 4).

EXAMPLE 5

Preparation of p-2-norbornylstyrene Represented by Formula 7

A styrene represented by Formula 7 was prepared using 1-(p-(2-bornyl)phenyl)ethanol in the same manner of Example 1 under the reaction condition given in Table 5.

The prepared styrene was identified by NMR and the result was as follows;

$^1$H NMR (CDCl$_3$): δ 143-1.50 (m, 7H), 1.76 (m, 2H), 1.88 (s, 1H), 2.78 (s, 1H), 5.18 (d, 1H), 5.61 (d, 1H), 6.63 (q, 1H), 7.10 (d, 2H), 7.25 (d, 2H)

(7)

TABLE 5

Preparation of p-2-norbornylstyrene under a variety of conditions

| Run | Alcohol (M) | p-Toluenesulfonic acid(mol %) | Reaction temperature (° C.) | Addition time (hr) | Reaction time after addition (hr) | Yield (%) |
|---|---|---|---|---|---|---|
| 1 | 0.2 | 2 | 110 | 1.1 | 0 | 90 |
| 2 | 0.2 | 1.5 | 110 | 1.1 | 0 | 92 |
| 3 | 0.5 | 1.5 | 110 | 1.1 | 0 | 75 |
| 4 | 0.2 | 5 | 110 | 1.1 | 0 | 63 |

As seen in Table 5, the yield was highest when a small amount of p-tolue-nesulfonic acid was used, as in Example 4 (Run 2).

EXAMPLE 6

Preparation of p-phenylstyrene Represented by Formula 8

A styrene represented by Formula 8 was prepared using 1-(biphenyl)-ethanol in the same manner of Example 1 under the reaction condition given in Table 6 below.

The prepared styrene was identified by NMR and the result was as follows;

$^1$H NMR (CDCl$_3$): δ 5.20 (d, 1H), 5.63 (d, 1H), 6.70 (q, 1H), 7.22 (t, 1H), 7.30 (d, 2H) 7.36 (d, 2H), 7.41 (d, 2H), 7.47 (d, 2H)

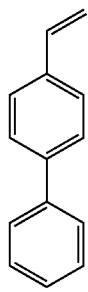

(8)

TABLE 6

Preparation of p-phenylstyrene under a variety of conditions

| Run | Alcohol (M) | p-Toluenesulfonic acid(mol %) | Reaction temperature (° C.) | Addition time (hr) | Reaction time after addition (hr) | Yield (%) |
|---|---|---|---|---|---|---|
| 1 | 0.2 | 2 | 110 | 1.1 | 0 | 70 |
| 2 | 0.2 | 4 | 110 | 1.1 | 0 | 93 |
| 3 | 0.5 | 4 | 110 | 1.1 | 0 | 80 |
| 4 | 0.2 | 4 | 110 | 0.5 | 0 | 76 |

As seen in Table 6, the yield was higher when a large amount of p-toluenesulfonic acid was used (Run 2).

EXAMPLE 7

Preparation of a Variety of Alkylstyrenes

A variety of styrenic derivatives having a long alkyl chain (C$_6$ or longer) or a sec- or tert-alkyl groups substituted in the benzene ring were prepared using 1-alkylphenyl-ethanol under the condition given in Table 7 below.

TABLE 7

Preparation of a variety of alkylstyrenes[a]

| Run | Alkyl group | Alcohol (M) | p-Toluenesulfonic acid (mol %) | Addition time (hr) | Yield (%) |
|---|---|---|---|---|---|
| 1 | p-n-Octyl | 0.2 | 2 | 1.1 | 90 |
| 2 | p-n-Decyl | 0.2 | 2 | 1.1 | 94 |
| 3 | p-n-Dodecyl | 0.2 | 2 | 1.0 | 93 |
| 4 | p-sec-Butyl | 0.2 | 1.5 | 1.1 | 92 |
| 5 | p-tert-Butyl | 0.2 | 1.5 | 1.0 | 96 |
| 6 | m-Methyl | 0.2 | 2 | 1.1 | 85 |
| 7 | m-Butyl | 0.2 | 2 | 1.1 | 87 |

[a]Reaction condition: reaction temperature = 110° C.; Reaction time after addition = 0 hr As seen in Table 7, the reaction of substituents at m-position on the benzene ring also proceeded, however, the reaction yield was higher at the p-position of the benzene ring than the m-position.

COMPARATIVE EXAMPLE 1

Preparation of alkylstyrene Represented by Formula 3

1-Phenyl-ethanol and an adequate amount of p-toluenesulfonic acid were dissolved in toluene in a two-neck flask equipped with a Dean-Stark trap. The reaction solution was heated from outside to create a reflux condition.

After the reaction was performed under the condition given in Table 8 below, the reaction was terminated in the same manner of Example 1. The product was purified to obtain a transparent and colorless styrene represented by Formula 3 below.

The prepared styrene was identified by NMR and the result was as follows;

$^1$H NMR (CDCl$_3$): δ 5.22 (d, 1H), 5.72 (d, 1H), 6.70 (q, 1H), 7.31 (m, 3H), 7.39 (d, 2H)

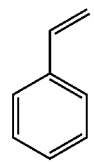

(3)

TABLE 8

Preparation of styrene under a variety of conditions

| Run | Alcohol (M) | p-Toluenesulfonic acid (mol %) | Reaction temperature (° C.) | Reaction time (hr) | Yield (%) |
|---|---|---|---|---|---|
| 1 | 0.1 | 2 | 25 -> 110 | 1 | 20 |
| 2 | 0.1 | 2 | 25 -> 110 | 2 | 30 |
| 3 | 0.2 | 2 | 25 -> 110 | 2 | 33 |
| 4 | 0.2 | 5 | 25 -> 110 | 2 | 45 |
| 5 | 0.2 | 10 | 25 -> 110 | 2 | 35 |
| 6 | 0.5 | 5 | 25 -> 110 | 1 | 38 |

As seen in Table 8, the yields of comparative example were low in all conditions, different from those of Example 1, in which the alcohol starting material and p-toluenesulfonic acid together were dissolved in toluene and the reaction was performed.

COMPARATIVE EXAMPLE 2

Preparation of Alkylstyrenes Represented by Formulas 4, 5 and 6

Alkylstyrenes represented by Formulas 4, 5 and 6 were prepared in the same manner of Comparative Example 1 under the reaction condition given in Table 9

-continued

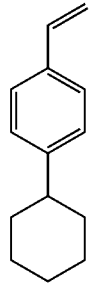

(6)

TABLE 9

Preparation of alkylstyrenes under a variety of conditions

| Run | Alkyl group | Alcohol (M) | p-Toluenesulfonic acid (mol %) | Reaction temperature (° C.) | Reaction time (hr) | Yield (%) |
|---|---|---|---|---|---|---|
| 1 | p-n-Butyl | 0.2 | 2 | 25 -> 110 | 1 | 40 |
| 2 | p-n-Butyl | 0.1 | 2 | 25 -> 110 | 2 | 33 |
| 3 | p-n-Hexyl | 0.1 | 2 | 25 -> 110 | 1 | 38 |
| 4 | p-n-Hexyl | 0.2 | 5 | 25 -> 110 | 1 | 30 |
| 5 | p-n-Cyc-ohexyl | 0.2 | 1.5 | 25 -> 110 | 1 | 40 |
| 6 | p-n-Cyc-ohexyl | 0.2 | 5 | 25 -> 110 | 1 | 28 |

The prepared styrene was identified by NMR and the result was as follows;

$^1$H NMR (CDCl$_3$): δ 0.75 (t, 3H), 1.15 (sextet, 2H), 1.41 (quintet, 2H), 2.41 (t, 2H) 5.01 (d, 1H), 5.52 (d, 1H), 6.52 (q, 1H), 6.97 (d, 2H), 7.17 (d, 2H) $^1$H NMR (CDCl$_3$): δ 0.88 (t, 3H), 1.28 (m, 6H), 1.60 (quintet, 2H), 2.58 (t, 2H), 5.18 (d, 1H), 5.68 (d, 1H), 6.69 (q, 1H), 7.13 (d, 2H), 7.30 (d, 2H) $^1$H NMR (CDCl$_3$): δ 1.30 (m, 1H), 1.46 (m, 4H), 1.78 (m, 1H), 1.88 (m, 4H), 2.53 (s, 1H), 5.21 (d, 1H), 5.73 (d, 1H), 6.73 (q, 1H), 7.20 (d, 2H), 7.37 (d, 2H)

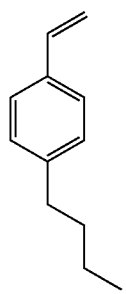

(4)

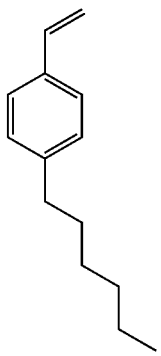

(5)

As seen in Table 9, the yields of comparative example were low in all conditions, different from those of Examples 2, 3 and 4, in which the alcohol starting material and p-toluenesulfonic acid together were dissolved in toluene and the reaction was performed under similar conditions to Examples 2, 3 and 4.

INDUSTRIAL APPLICABILITY

As apparent from the above description, when the method for preparing a styrenic olefin according to the present invention is applied to synthesis of medicines or natural products, homopolymerization or copolymerization of styrenic polymers, etc., generation of byproducts may be minimized and styrenic olefins having a variety of substituents may be obtained in high yield.

While the present invention has been described in detail with reference to exemplary embodiments thereof, it will be understood by those skilled in the art that various modifications and substitutions an be made thereto without departing from the spirit and scope of the present invention as defined in the appended claims.

The invention claimed is:

1. A method for preparing a styrenic olefin comprising the steps of:
    adding a catalyst and a solvent in a reactor and heating the reactor to create a reflux state;
    adding an alcohol starting material dropwise to the reactor at a constant rate;
    removing water generated by adding the alcohol starting material from the reactor; and
    purifying the obtained styrenic olefin,
    wherein the alcohol starting material is a material represented by the following Formula 1:

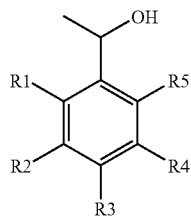

(1)

where each of R1, R2, R3, R4 and R5, which may be identical or different, may be selected from the group consisting of a hydrogen atom, a halogen group, a hydroxy group, a thio group, an amine group, an alkyl group, a cycloalkyl group, a haloalkyl group, an alkylsilyl group, a silylalkyl group, an alkoxy group, a alkylthio group and an alkylamine group having 1-20 carbon atoms and an aryl group, a haloaryl group, an arylalkyl group, an alkylaryl group, an arylsilyl group, a silylaryl group, an arylalkylsilyl group, an aryloxy group, an arylthio group and an arylamine group having 6-40 carbon atoms.

2. The method of claim 1, wherein the catalyst is at least one selected from the group consisting of acetic acid, haloacetic acid, phosphoric acid, hydrochloric acid, sulfuric acid, an alkylsulfonic acid, an arylsulfonic acid, an alkylarylsulfonic acid, a haloarylsulfonic acid, an alkylhaloarylsulfonic acid, an alkylcarboxylic acid, an arylcarboxylic acid, a haloalkylcarboxylic acid, a haloarylcarboxylic acid and an alkylhaloarylcarboxylic acid having 1-20 carbon atoms.

3. The method of claim 1, wherein the catalyst is comprised in 0.1-20 mol % per 100 mol % of the alcohol starting material.

4. The method of claim 1, wherein the solvent is at least one selected from the group consisting of an alkane, a cycloalkane, an arene, an alkylarene, a haloalkane, a halocycloalkane, a haloarene and an alkylhaloarene having 1-20 carbon atoms.

5. The method of claim 1, wherein the alcohol starting material is comprised in 0.05-5 M.

6. The method of claim 1, wherein the reaction temperature of the step of creating the reflux state is 50-200° C.

7. The method of claim 1, wherein the final addition time of the step of adding the alcohol starting material dropwise is 0.1-4 hours.

8. The method of claim 1, wherein reaction is performed for 2 hours or less after the alcohol starting material has been added finally.

9. The method of claim 1, wherein the water is removed by distilling and/or using a drying agent.

10. The method of claim 9, wherein the drying agent is at least one selected from the group consisting of anhydrous magnesium sulfate ($MgSO_4$), anhydrous calcium sulfate ($CaSO_4$), anhydrous magnesium chloride ($MgCl_2$), anhydrous calcium chloride ($CaCl_2$), alumina ($Al_2O_3$) and silica gel ($SiO_2$).

11. The method of claim 1, wherein the purification is performed by distilling and/or passing through an alumina or silica gel column.

12. The method of claim 11, wherein the distillation is performed by simple distillation and/or vacuum distillation.

13. The method of claim 11, wherein the distillation is performed at 25-400° C.

14. The method of claim 11, wherein the distillation is performed at a degree of vacuum of $0.5\text{-}10^{-6}$ atm.

* * * * *